United States Patent
Sathe et al.

(10) Patent No.: US 10,414,720 B2
(45) Date of Patent: Sep. 17, 2019

(54) PROCESS FOR THE PREPARATION OF LACOSAMIDE

(71) Applicant: UNICHEM LABORATORIES LTD, Mumbai, Maharashtra (IN)

(72) Inventors: Dhananjay G. Sathe, Maharashtra (IN); Arijit Das, Goa (IN); Sanjay Raikar, Goa (IN); Rahul Bhagwatkar, Maharashtra (IN); Ramdas Ahire, Maharashtra (IN)

(73) Assignee: Unichem Laboratories Ltd., Mumbai (IN)

( * ) Notice: Subject to any disclaimer, the term of this patent is extended or adjusted under 35 U.S.C. 154(b) by 0 days.

(21) Appl. No.: 16/076,486

(22) PCT Filed: Jun. 12, 2017

(86) PCT No.: PCT/IB2017/053448
§ 371 (c)(1),
(2) Date: Aug. 8, 2018

(87) PCT Pub. No.: WO2018/060781
PCT Pub. Date: Apr. 5, 2018

(65) Prior Publication Data
US 2019/0047944 A1    Feb. 14, 2019

(30) Foreign Application Priority Data
Sep. 28, 2016   (IN) .............. 201621033097

(51) Int. Cl.
C07C 231/02   (2006.01)
C07C 269/04   (2006.01)
C07C 269/06   (2006.01)
C07C 237/00   (2006.01)
C07B 51/00    (2006.01)
C07C 237/22   (2006.01)

(52) U.S. Cl.
CPC .......... *C07C 231/02* (2013.01); *C07C 237/00* (2013.01); *C07C 269/04* (2013.01); *C07C 269/06* (2013.01); *C07B 51/00* (2013.01); *C07C 237/22* (2013.01)

(58) Field of Classification Search
None
See application file for complete search history.

(56) References Cited

U.S. PATENT DOCUMENTS

| 9,718,765 B1 * | 8/2017 | Chen ............ C07C 269/06 |
| 2009/0298947 A1 * | 12/2009 | Mundorfer .......... A61K 31/165 514/616 |
| 2013/0123537 A1 * | 5/2013 | Garimella ........... C07C 231/12 564/158 |

FOREIGN PATENT DOCUMENTS

| IN | 2011MU00893 | * 11/2012 | |
| WO | 2011095995 | 8/2011 | |
| WO | 2012001710 | 1/2012 | |
| WO | WO-2012051551 A1 * | 4/2012 | .......... C07D 235/22 |

OTHER PUBLICATIONS

International Search Report and Written Opinion dated Aug. 25, 2017, issued in PCT/IB2017/053448.

* cited by examiner

*Primary Examiner* — Amy C Bonaparte
(74) *Attorney, Agent, or Firm* — Kilpatrick Townsend & Stockton LLP

(57) ABSTRACT

The present invention relates to an improved process for the synthesis of (R)-Lacosamide in which free base of O-methyl-N-benzyl-D-Serinamide is not isolated before acylation. The process avoids the use of column chromatography and chiral resolution for the preparation of different stages of Lacosamide.

6 Claims, No Drawings

PROCESS FOR THE PREPARATION OF LACOSAMIDE

FIELD OF INVENTION

The present invention relates to an improved process for the synthesis of (R)-Lacosamide in which free base of O-methyl-N-benzyl-D-Serinamide is not isolated before acylation.

BACKGROUND OF THE INVENTION

Lacosamide chemically known as (R)—N-benzyl-2-acetamido-3-methoxypropionamide or (2R)-2-(acetylamino)-3-methoxy-N-(phenylmethyl)propanamide as shown in Formula I. It is an amino acid derivative having analgesic and anticonvulsant property.

Formula I

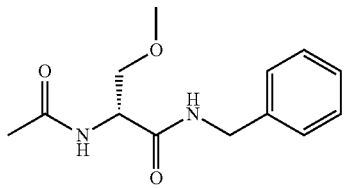

Lacosamide was developed by Union Chimique Belge (UCB) Pharma and is marketed under brand name Vimpat. It was approved by USFDA in October 2008 as an adjunctive therapy in the treatment of partial-onset seizures in patients with epilepsy aged 17 years and older.

Several methods and Schemes have been developed and disclosed in prior art, for the preparation of lacosamide. Lacosamide has been disclosed for the first time in the U.S. Pat. No. 5,773,475 (Now Reissued as U.S. RE38551) by Research Corporation Technologies. According to this patent, lacosamide is prepared in three different methods which is described below.

Scheme-1:

D-Serine (II) was esterified under acidic condition with methanol, to provide the corresponding ester (III) which was reacted with benzylamine to form the corresponding amide (W). Acylation of the free amino group with acetic anhydride and chiral resolution provide compound (V). O-methylation of (V) using methyl iodide in presence of silver oxide yields Lacosamide (I) in about 4 days when the reaction is carried out at room temperature, as illustrated in example 1 column 12, lines 9-13.

Scheme-1

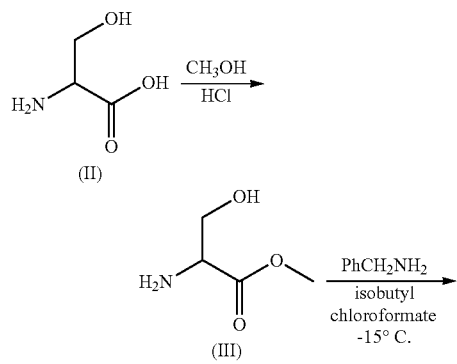

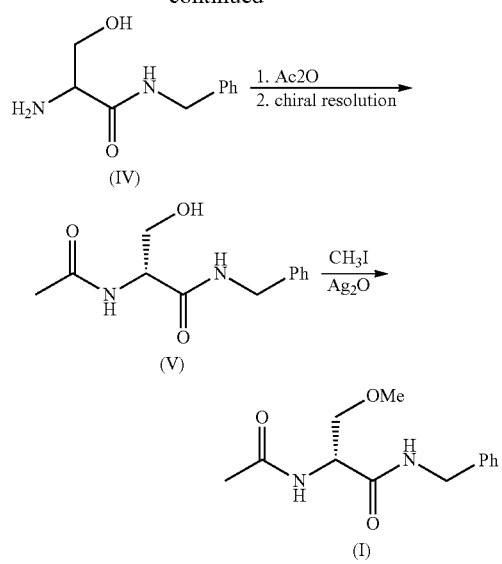

This method suffers from several disadvantages such as loss of material during resolution and use of hazardous reagents such as methyl iodide and expensive ones such as silver oxide. All these factors combined together makes it unsuitable for the large scale manufacturing of Lacosamide.

Scheme-2:

In this scheme acetylation of D-serine (VI) was carried out using acetic anhydride in acetic acid to give N-acetyl-D-serine (VII), which on treatment with isobutyl chloroformate in presence of N-methylmorpholine in tetrahydrofuran at −78° C., followed by reaction with benzylamine to yield (2R)-2-acetamido-N-benzyl-3-hydroxypropanamide (V). Compound V was purified by flash column chromatography and followed by alkylation with methyl iodide in the presence of silver oxide in acetonitrile to provide Lacosamide (I). This methylation was carried out at room temperature for 4 days as illustrated in example 2(b), column 13, lines 1-5

Scheme-2

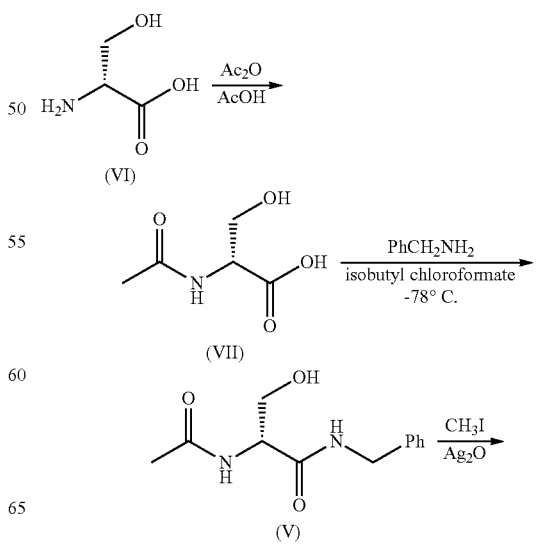

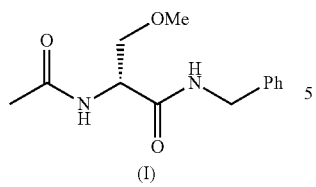

Use of column chromatography is time consuming normally not used in plants and low temperature of −78° C. is difficult on plant scale.

Scheme-3:

This scheme comprises amino group protection of D-serine with benzyloxycarbonyl chloride to yield N-Benzyloxycarbonyl-D-serine (VIII), which on alkylation using methyl iodide in the presence of silver oxide in acetonitrile yields (2R)-methyl-2-(benzyloxycarbonylamino)-3-methoxypropanoate (IX) which was purified by flash column chromatography and hydrolyzed to give (2R)-2-(benzyloxycarbonylamino)-3-methoxypropanoic acid (X). Conversion of VIII to IX was carried out at room temperature for 24 hours as illustrated in example 5(b), lines 34-38. Compound (X) was treated with isobutyl chloroformate −78° C. in THF in presence of N-methylmorpholine followed by reaction with benzylamine to yield the compound (2R)-benzyl 1-(benzylamino)-3-methoxy-1-oxopropan-2-ylcarbamate (XI). Deprotection of N-protecting group provides free amine which was subsequently acetylated with acetic anhydride in the presence pyridine and DMAP to give crude Lacosamide (I) which was purified by flash column chromatography to give pure Lacosamide (I).

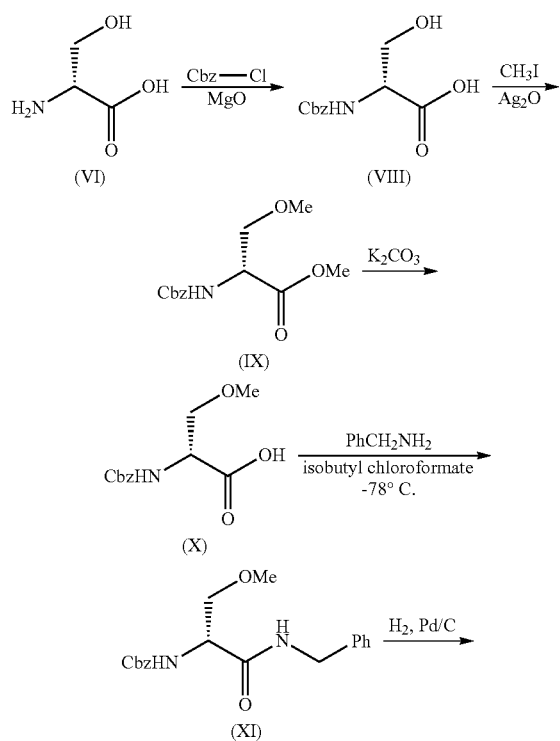

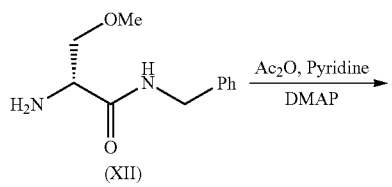

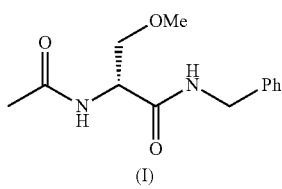

Above scheme suffers from various drawbacks such as lengthy synthesis, use of column chromatography for the purification of intermediate and final product, reactions at low temperature (−78° C.), unstable intermediate (compound XII) and.

Various processes are also known in the literature for the synthesis of Lacosamide. U.S. Pat. No. 7,884,134 discloses a process for the preparation of Lacosamide of Formula-I which includes O-methylation of N-Boc-D-serine (XIII) using dimethyl sulfate in presence of butyl lithium or with dimethyl sulfate using phase-transfer catalyst and sodium hydroxide to obtain compound XIV. Conversion of compound XIII to XIV was carried out at less than −10° C. Reaction mixture was aged at 0-5° C. for 9 hours as illustrated by example 1 in column 10-11. Compound XIV was reacted with benzylamine using mixed anhydride method disclosed earlier to get the compound (2R)-tert-butyl 1-(benzylamino)-3-methoxy-1-oxopropan-2-ylcarbamate (XV). Deprotection of the compound XV with hydrochloric acid yields the compound (2R)-2-amino-N-benzyl-3-methoxy-propanamide (XII), which on acetylation yields the compound Lacosamide of Formula-I. The reaction sequence is as given in Scheme-4.

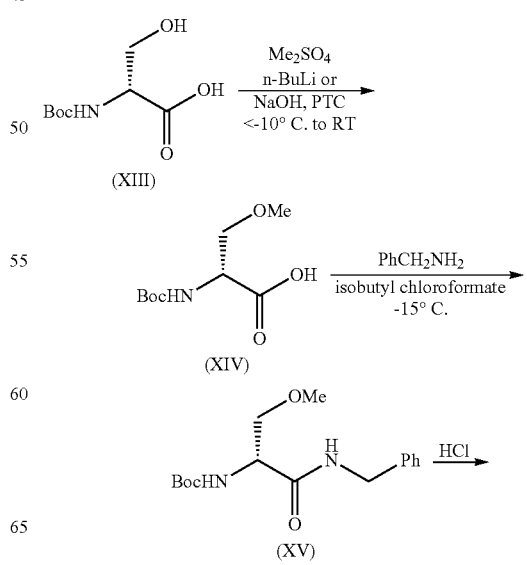

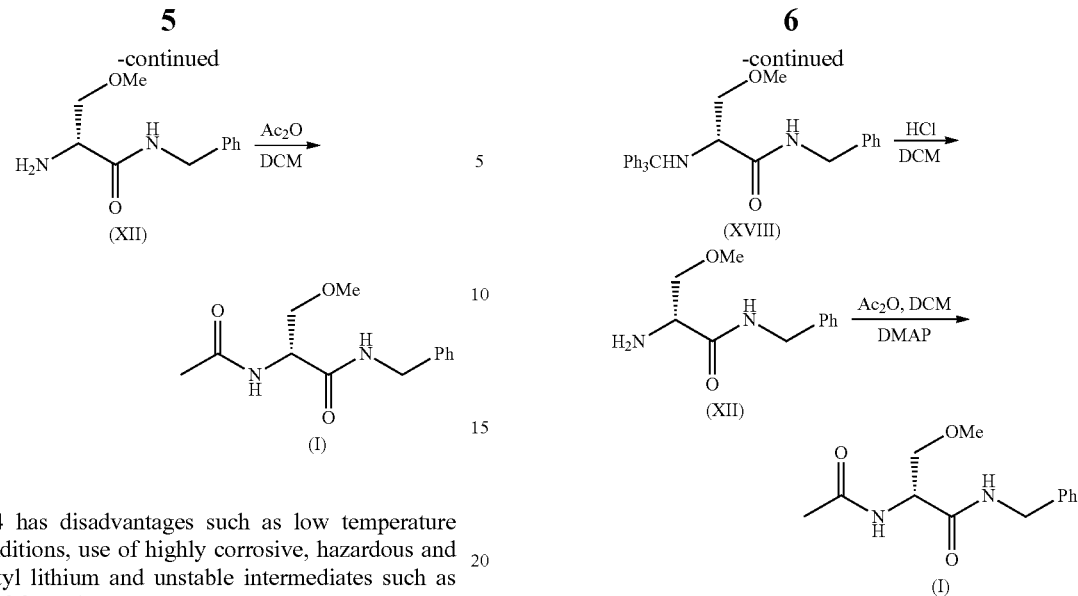

Scheme 4 has disadvantages such as low temperature reaction conditions, use of highly corrosive, hazardous and costly n-Butyl lithium and unstable intermediates such as compound of formula XII.

U.S. Pat. No. 8,093,426 discloses a process for preparation of Lacosamide of Formula-I which involves protection of hydroxyl group of D-serine using trimethylsilyl chloride followed by protection of amino group with trityl chloride and subsequently deprotecting hydroxyl group to isolate N-trityl-D-serine (XVI). Compound XVI is reacted with methyl iodide in the presence of sodium hydride and imidazole at −15 to −5° C. for about 3 hours, to obtain O-methyl-N-trityl-D-serine (XVII) followed by reaction of XVII with isobutyl chloroformate in presence of N-methylmorpholine at −15° C. and reaction with benzylamine to yield (2R)—N-benzyl-3-methoxy-2-(tritylamino)propanamide (XVIII). Compound XVIII on deprotection yields (2R)-2-amino-N-benzyl-3-methoxy-propanamide XII, which on acetylation with acetic anhydride in the presence of dimethylaminopyridine yields Lacosamide of Formula-I. The reaction sequence is given in Scheme-5.

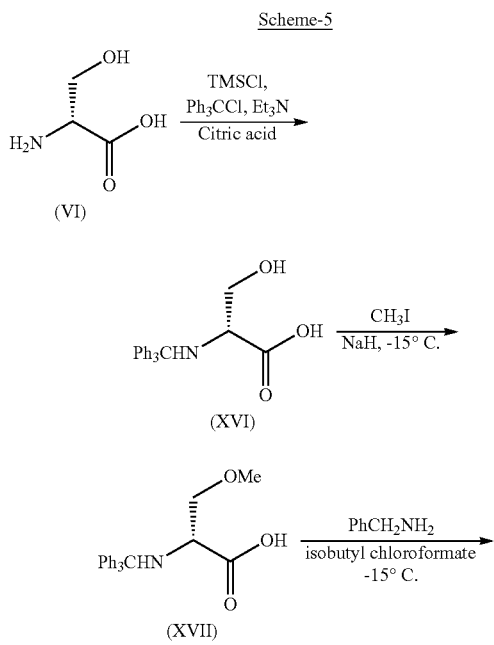

This synthetic sequence suffers drawbacks such as lengthy process, lower temperature for carrying out amidation reaction, use of hazardous Methyl iodide. All these factors pose serious practical problems for large scale production. Although the overall yield is not described in U.S. Pat. No. 8,093,426, it is very low and is about 16%.

WO2014068333 disclosed a method for the preparation of Lacosamide wherein the racemic compound XIX was subjected to kinetic resolution using N-formyl-L-leucine followed by N-acetylation with isopropyl acetate in presence of sodium acetate to obtain Lacosamide (Scheme-6).

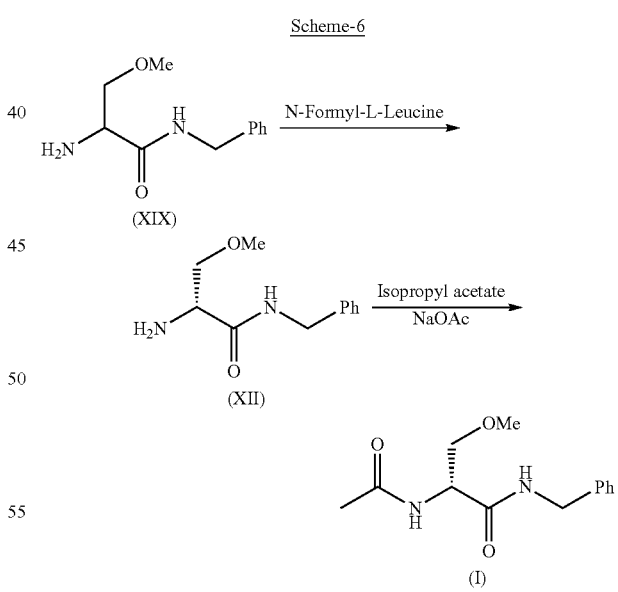

This approach also suffers from disadvantages such as loss of 50% material during resolution, use of costly resolving agent and lower yield in acetylation stage. Moreover, the final product obtained was purified using Dean-stark assembly which is a tedious method and not suitable for large scale.

In the method described by U.S. Pat. No. 8,907,132, (R)-2-amino-N-benzyl-3-hydroxypropanamide (IV) was reacted with acetic anhydride in DCM to yield compound (V) which on treatment with dimethyl sulphate in toluene and aq. NaOH under phase transfer condition give Lacosamide (I). The reaction sequence is depicted in Scheme 7. No methodology or means are described by U.S. Pat. No. 8,907,132 to understand when the reaction of conversion of V to I would get over, although the reaction necessitates the use of Phase transfer catalyst (PTC).

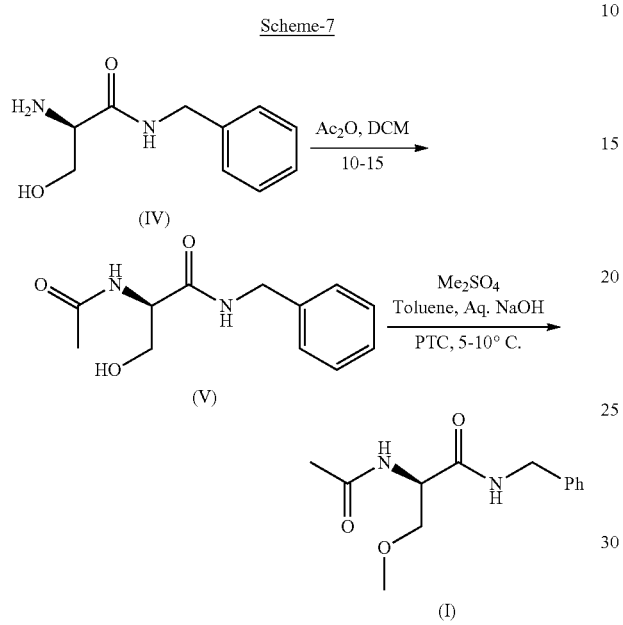

Although the overall yield is not described in U.S. Pat. No. 8,907,132, it is very low and is about 33%. The sequence teaches a reaction to prepare N-Boc-D-serine at 20-25° C. after stirring for 10 hours.

In 893/MUM/2011, D-serine was converted to N-Boc-D-Serine in water, 1,4-dioxane mixture under basic condition using Boc-anhydride. Compound XIII was treated with isobutyl chloroformate and benzyl amine to yield compound (XX) which is subsequently subjected to O-methylation using dimethyl sulphate under phase transfer conditions to give compound (XV), the duration of the reaction being 14 hours as illustrated in example step 3. This was further deprotected using conce. HCl and the free base was converted to its acyl derivative i.e Lacosamide. The reaction sequence is depicted in Scheme-8.

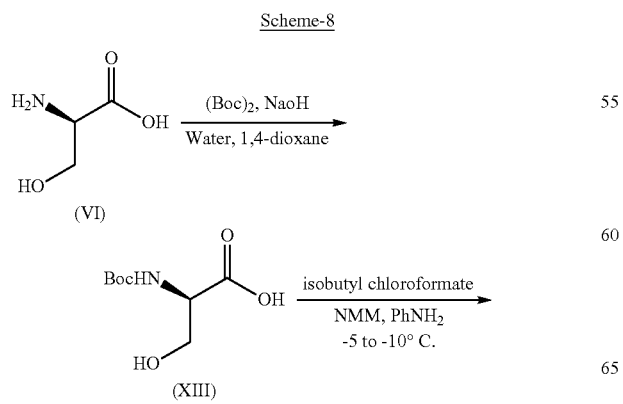

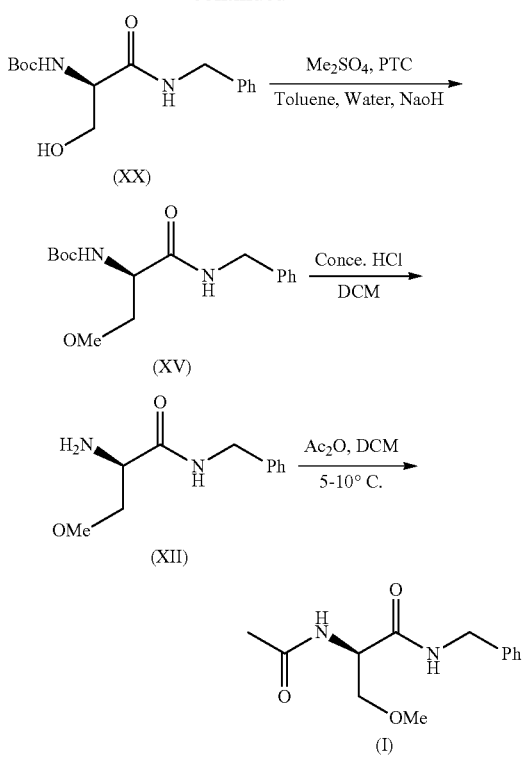

Above sequence suffers from long reaction time like 14 hours to prepare N-Boc-D-serine (compound XIII), subzero temperatures in the amidation reaction and isolation of free base (compound XII).

U.S. Pat. No. 8,796,488 describes a process to prepare lacosamide in which racemic N-acyl-D-serine (XXIII) was reacted with benzyl amine in THF to yield compound of formula (XXIV) which on methylation using methyl p-toluene sulphonic acid in THF and aq. NaOH gives compound (XXV). This conversion necessitates the use of PTC. N-acyl protection of Compound of formula (XXV) was deprotected suing dil. HCl in DCM to yield (XXVI) which on chiral resolution gives chiral salt as shown in compound (XXVII). Compound (XXVII) is acylated using acetic anhydride in tert-butyl methyl ether to give Lacosamide (I). The reaction scheme is depicted in Scheme-9.

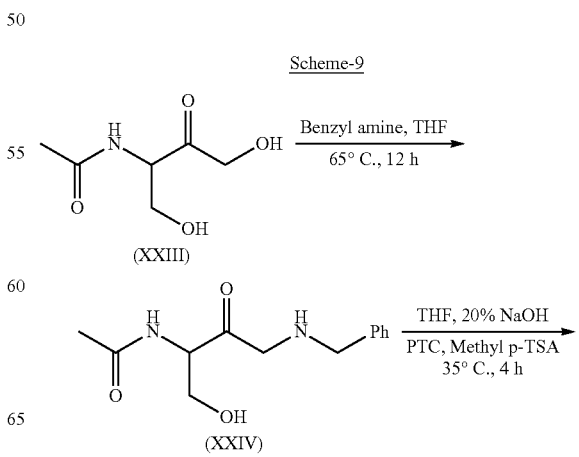

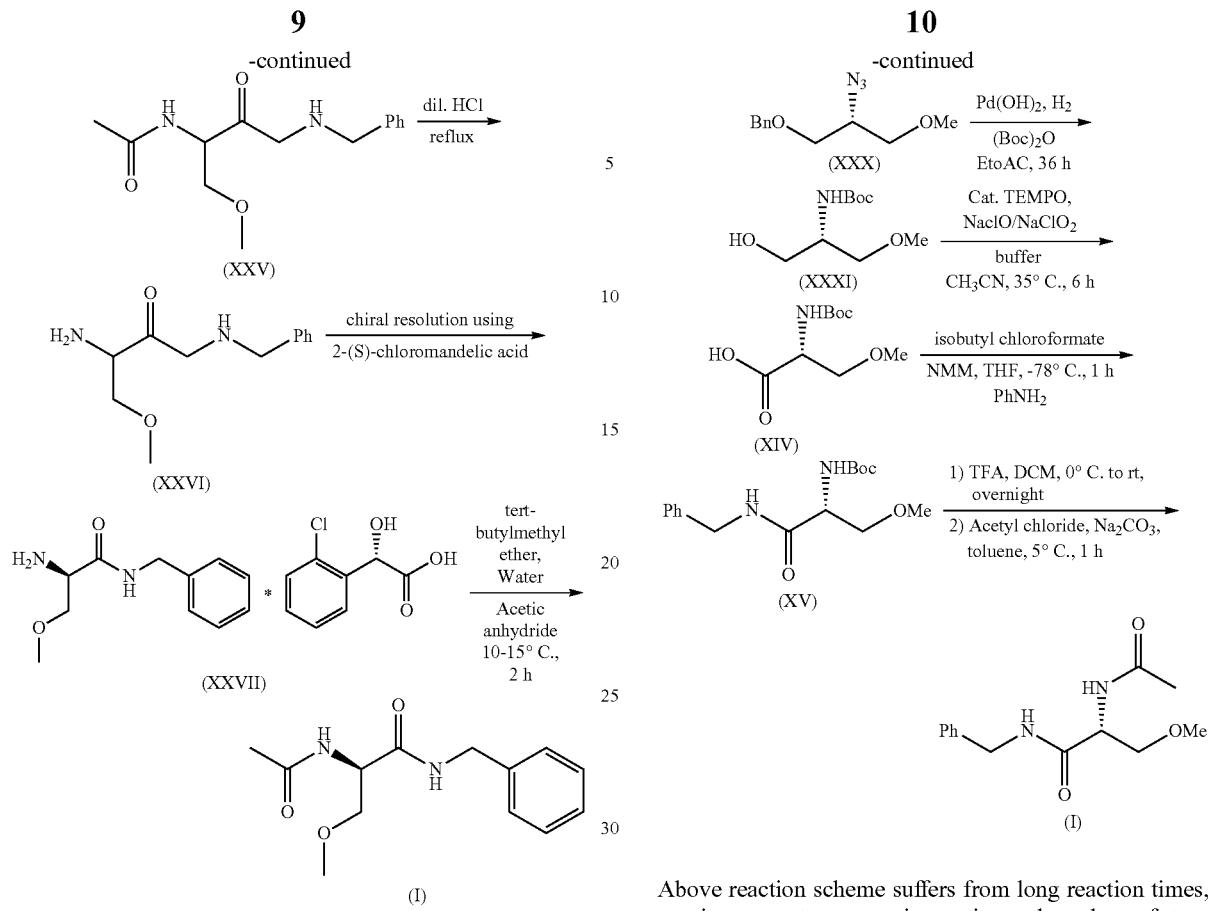

Drawbacks of this sequence are loss of material during chiral resolution, long reaction times and expensive chiral agents like 2-(S)-chloromandelic acid and which makes above sequence of reaction unsuitable for the scale up.

U.S. Pat. No. 8,748,660 describes a process in which (S)-benzylglycidyl ether (XXVIII) is regioselectively opened under basic condition in methanol to give compound (XXIX) which in turn is converted to azide derivate (XXX) using diisopropyl azadicarboxylate, triphenyl phosphine and diphenylphosphoryl azide in toluene. The azide derivative (XXX) on reduction using $Pd(OH)_2$ and Hydrogen gas in presence of Boc-anhydride yields compound (XXXI). Compound of formula (XXXI) on oxidation with sodium hypochlorite in presence of catalytic TEMPO in acetonitrile give compound (XIV) which on reaction with isobutyl chloroformate, NMM and benzyl amine in THF at −78° C. gives compound (XV). Compound of formula (XV) was deprotected using TFA in DCM and subsequently acylated using acetic anhydride in presence of sodium carbonate in toluene to give Lacosamide (I). The reaction sequence is depicted in Scheme-10.

Scheme-10

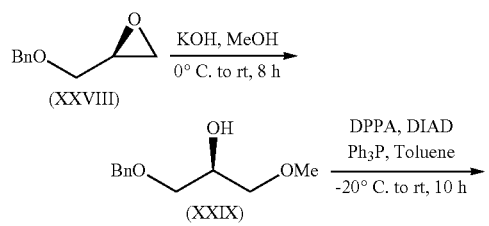

Above reaction scheme suffers from long reaction times, expensive reagents, cryogenic reaction and numbers of steps involved, rendering it not so suitable for large scale production.

In view of the preparation methods available for lacosamide and considering the pitfalls of the prior art in which complex methodologies are applied, there is a need for simple and cost effective process for the preparation of lacosamide that eliminates racemization of intermediate compounds and provides improved efficiency per reaction volume in terms of yield, purity and chiral purity.

OBJECT OF THE INVENTION

The main object of the present invention is to provide an improved process for the synthesis of (R)-Lacosamide in which free base of O-methyl-N-benzyl-D-Serinamide is not isolated before acylation.

Another object of the present invention is to provide an improved process for the synthesis of Lacosamide (Formula-I) with a better overall yield, better chiral purity and starting from very basic and cheap raw material i.e. D-serine which is commercially available.

Yet another object of the present invention is to provide a cost effective, environment friendly and economically viable process to prepare Lacosamide.

Yet another object of the present invention is to avoid column chromatography and chiral resolution for the preparation of different stages of Lacosamide.

Yet another object of the present invention is to avoid use of hazardous, pyrophoric, flammable reagents and cryogenic conditions for the large scale production of Lacosamide.

Yet another object of the present invention is to avoid use of reagents such as isobutyl chloroformate, which result in emulsion formation during work-up.

SUMMARY OF THE INVENTION

There is provided an improved process for the synthesis of (R)-Lacosamide in which free base of O-methyl-N-benzyl-D-Serinamide is not isolated before acylation.

There is also provided an improved process for the synthesis of Lacosamide (Formula-I) with a better overall yield and starting from very basic and cheap raw material i.e. D-serine which is commercially available.

There is provided a simple, cost effective, environment friendly and economically viable process to prepare Lacosamide suitable for large scale production.

The process provided as per the present invention avoids column chromatography and chiral resolution for the preparation of different stages of Lacosamide.

The process provided in the present invention avoids use of reagents such as isobutyl chloroformate, which result in emulsion formation during work-up.

The present invention provides the process as depicted in Scheme-11 and it comprises of:

1. A process for the preparation of Lacosamide compound of the formula (I) comprising:

i) N-Boc protection of D-serine at 50° C. for the duration of 1-2 hours using Boc-anhydride in presence of sodium hydroxide as a base and water as a solvent to obtain N-Boc-D-serine, ii) Coupling of carboxylic acid moiety of N-Boc-D-serine produced in step i), with benzyl amine in presence of ethyl chloroformate and N-methyl morpholine at 10 to 15° C. to obtain tert-butyl [(2R)-1-(benzylamino)-3-hydroxy-1-oxopropan-2-yl]carbamate, iii) O-methylation of tert-butyl[(2R)-1-(benzylamino)-3-hydroxy-1-oxopropan-2-yl]carbamate produced in step ii), with dimethyl sulfate in presence of potassium hydroxide as a base and dichloromethane as a solvent in the absence of PTC to generate tert-butyl [(2R)-1-(benzylamino)-3-methoxy-1-oxopropan-2-yl]carbamate, iv) Hydrolysis of the N-Boc group of the tert-butyl [2R)-1-(benzylamino)-3-methoxy-1-oxopropan-2-yl]carbamate produced in step iii) with an alcoholic HCl at 50° C. to produce a hydrochloride salt of (R)-2-amino-N-benzyl-3-methoxypropanamide and subsequent N-acetylation of the hydrochloride salt of (R)-2-amino-N-benzyl-3-methoxypropanamide in the presence of sodium acetate without isolating free base (R)-2-amino-N-benzyl-3-methoxypropanamide, to produce Lacosamide having the chemical name (2R)-2-(acetylamino)-N-benzyl-3-methoxy propanamide.

Scheme 11

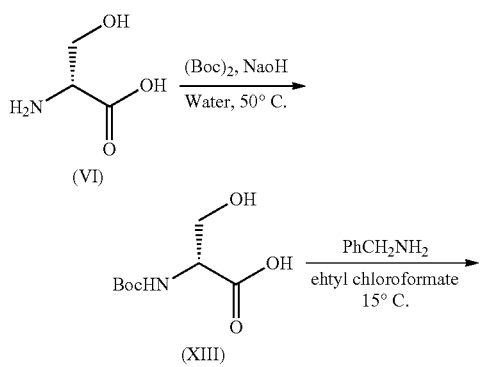

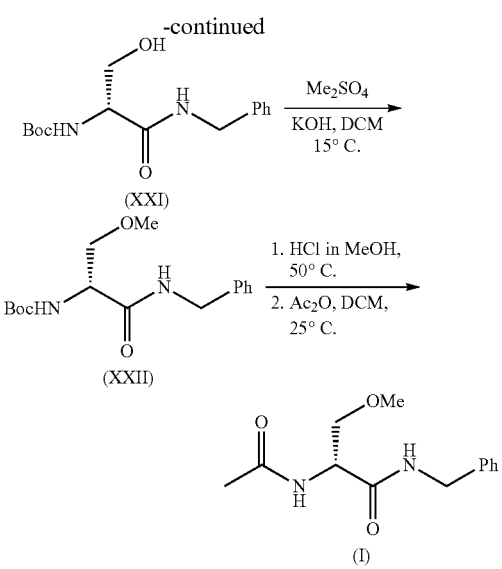

Purification of the crude Lacosamide was carried out using a mixture of ethyl acetate and heptane. Solvent ratio of ethyl acetate in the range of n-Heptane is 2:1 to 1:2 provides acceptable results. The relative quantities of the two solvents were optimized and 3 volumes each was found to give best results.

DETAILED DESCRIPTION OF THE INVENTION

There is provided a novel and non-obvious process to prepare (R)-Lacosamide from different substrates and different reaction conditions. There is provided an improved process for the synthesis of (R)-Lacosamide in which free base of O-methyl-N-benzyl-D-Serinamide is not isolated before acylation.

The present invention provides the cost effective, environment friendly and economically viable process to prepare (R)-Lacosamide which does not use column chromatography and chiral resolution for the preparation of different stages.

The process is improved process because Lacosamide (Formula-I) with a better overall yield is prepared from very basic and cheap raw material i.e. D-serine which is commercially available. Thus the process is economical also.

The process of the present invention is depicted in Scheme-11.

A process for the preparation of Lacosamide compound of the formula (I) comprising:

i) N-Boc protection of D-serine at 50° C. for the duration of 1-2 hours using Boc-anhydride in presence of sodium hydroxide as a base and water as a solvent to obtain N-Boc-D-serine, ii) Coupling of carboxylic acid moiety of N-Boc-D-serine produced in step i), with benzyl amine in presence of ethyl chloroformate and N-methyl morpholine at 10 to 15° C. to obtain tert-butyl[(2R)-1-(benzylamino)-3-hydroxy-1-oxopropan-2-yl]carbamate, iii) O-methylation of tert-butyl[(2R)-1-(benzylamino)-3-hydroxy-1-oxopropan-2-yl]carbamate produced in step ii), with dimethyl sulfate in presence of potassium hydroxide as a base and dichloromethane as a solvent in the absence of PTC to generate tert-butyl [(2R)-1-(benzylamino)-3-methoxy-1-oxopropan-2-yl]carbamate, iv) Hydrolysis of the N-Boc group of the tert-butyl [2R)-1-(benzylamino)-3-methoxy-1-oxopropan-2-yl]carbamate produced in step iii) with an alcoholic HCl at 50° C. to produce a hydrochloride salt of (R)-2-amino-N-benzyl-3-methoxypropanamide and subsequent N-acetylation of the hydrochloride salt of (R)-2-amino-N-benzyl-3-methoxypropanamide in the presence of sodium acetate without isolating free base (R)-2-amino-N-benzyl-3-methoxypropanamide, to produce Lacosamide having the chemical name (2R)-2-(acetylamino)-N-benzyl-3-methoxy propanamide.

The process begins with amine protection of D-Serine using Boc anhydride in presence of suitable base and a suitable solvent. Typical, non-limiting examples of base include potassium hydroxide, sodium hydroxide, lithium hydroxide, potassium carbonate, sodium carbonate, sodium bicarbonate, triethyl amine, diisopropyl amine and pyridine. The solvents include dioxane, water, tetrahydrofuran, dimethyl formamide and mixtures thereof. More particularly, aqueous solution of sodium hydroxide was engaged to obtain best results in terms of yield and purity. The reaction was carried out by adding D-serine to a solution of sodium hydroxide in water, followed by addition of Boc anhydride at ambient temperature (25-30° C.). The reaction mixture was heated at 50° C. for 2 h or at ambient temperature for 16 h. After completion of the reaction that was monitored by TLC, the reaction mixture was washed with ethyl acetate to get rid of unreacted D-serine and other minor impurities. The pH of the reaction mixture was adjusted to 3-4 and the product was extracted with ethyl acetate.

Literature discloses that Boc-protection of D-serine can be carried out at room temperature, in about 16-20 hours. U.S. Pat. No. 8,907,132, scheme 7, page 5-6 teaches preparation of N-Boc-D-serine at 20-25° C. after stirring for 10 hours. Surprisingly it was noticed that N-Boc-D-serine can be prepared in just 1-2 h if the reaction temperature is maintained at 50° C.

Above ethyl acetate layer containing N-Boc-D-serine was subjected to mixed anhydride formation using alkyl chloroformate in presence of a suitable base. Alkyl chloroformate used may include but not limited to ethyl chloroformate, isopropyl chloroformate and isobutyl chloroformate. The use of base for this reaction could include but not limited to N-methyl pyrrolidine, N-methyl morpholine, triethyl amine, pyridine and diisopropyl ethyl amine. The choice of solvent other than ethyl acetate could include dichloromethane, tetrahydrofuran, diethyl ether, acetonitrile and dimethyl formamide. More particularly, the solution of Boc-D-serine in ethyl acetate, obtained from the previous step was treated with ethyl chloroformate in presence of N-methyl morpholine to get the mix anhydride which on treatment with benzyl amine at 10-15° C. gave tert-butyl [(2R)-1-(benzylamino)-3-hydroxy-1-oxopropan-2-yl]carbamate (XXI). Use of some alkyl chloroformates mainly isobutyl chloroformate leads to formation of emulsion during work up. This is undesirable. Surprisingly there was no emulsion formation when ethyl chloroformate was used.

In the prior art the amidation reaction is done at subzero temperatures ranging from −15° C. to −78° C. as depicted in the schemes 1, 2, 3, 4 and 5 drawn above. In scheme 8 it is below zero deg. Centigrade. Surprisingly in the present invention the reaction was carried out in a range of 0-5° C. Thus the inventive step resides in the reaction temperature which is well above zero unlike prior art.

Intermediate XXI was treated with dimethyl sulfate in presence of a suitable base and a solvent below 15° C. Typical, non-limiting examples of base include sodium hydroxide, potassium hydroxide, sodium hydride and diisopropyl ethyl amine, and that of solvent include acetonitrile, tetrahydrofuran and methylene dichloride. Preferably, potassium hydroxide was used as a base in dichloromethane as a solvent. The reaction was carried out by adding potassium hydroxide to a solution of intermediate XXI in dichloromethane at 5 to 15° C., followed by dimethyl sulfate. The reaction mass was stirred for 30-40 min below 15° C. The reaction mixture was washed with water and the organic layer was distilled under vacuum to obtain intermediate XXII.

In the prior art, in 0-methylation stage has often employed hazardous reagent like methyl iodide is used which is very volatile (boiling point: 42° C.) and expensive ones like silver oxide e.g. Scheme 1-3; Scheme 5. Others like scheme-4 used highly corrosive reagents like n-butyl lithium at subzero temperatures. Surprisingly the present invention does not use hazardous volatile reagent like methyl iodide or does not employ subzero temperatures. Reaction scheme 7 necessitates the use of PTC. There is no mention of how much time would be required nor is there mention of how to know if the reaction is complete. Reaction scheme 8 also employees phase transfer catalyst (PTC) in the O-Methylation reaction. Same is illustrated in example—Step 3 of 893/MUM/2011. After employing PTC the reaction is complete in 3-7 hours as per claims. The same reaction in step 3 is taught to take 14 hours at 5-10° C. Whereas the present invention does not use PTC and yet the reaction is complete in 3-5 hours. Schemes 1-3 require at least 24 hours to about 4 days to complete the reaction at room temperature. In the present invention the reaction was successfully carried out at 10-15° C. in 3-5 hours. Reaction scheme 9 also necessitates the use of PTC. Thus O-methylation step in the present invention is novel and non-obvious.

Boc-deprotection of intermediate XXII was carried out by reacting it with methanolic HCl at temperature ranging from 20 to 50° C., preferably at 40 to 50° C. The reaction mixture was evaporated under vacuum to obtain the hydrochloride salt of free base. Suitable solvent was added to the product followed by sodium acetate and dropwise addition of acetic anhydride to avoid exotherm. The use of solvent for this reaction could include but not limited to dichloromethane, acetonitrile, dimethyl formamide and tetrahydrofuran. More preferably, dichloromethane was used and the reaction mass was stirred for 2-3 h. The reaction mass was washed with water and the organic layer was evaporated under reduced pressure. Ethyl acetate (3 V) was added to the residue and the mixture was heated at 50-55° C. and n-heptane (5 V) was added under stirring. The reaction mixture was cooled to 10° C. for complete precipitation of the product. The precipitated product was filtered and dried under vacuum to obtain crude Lacosamide (I).

In the prior art after deprotection of N-Boc group, $NH_2.HCl$ salt was prepared. Prior art teaches base treatment to the salt to prepare free amine and to isolate it. Prior art teaches acylation of so generated free amine to give Lacosamide. Surprisingly, in the present invention, Lacosamide was prepared by direct acylation of $NH_2HCl$ salt by acetic anhydride in presence of sodium acetate. Here also resides the novelty and inventive step of the present invention.

Purification of the crude Lacosamide was carried out using a mixture of ethyl acetate and heptane. Solvent ratio of ethyl acetate in the range of n-Heptane is 2:1 to 1:2 provides acceptable results. The relative quantities of the two solvents were optimized and 3 volumes each was found to give best results. The purification process was carried out by adding ethyl acetate to the crude Lacosamide and heating the mixture to 50-55° C. n-Heptane was added; the mixture was stirred for 30-40 min and cooled to 10° C. to ensure complete precipitation of the product. The precipitated product was filtered under reduced pressure and dried in vacuum to obtain Lacosamide in pure form. Novelty and non-obviousness of the step of purification resides in the use of Lacosamide used for purification that was produced by the process described in the present invention.

The novelty and the non-obviousness of the process resides in multiple aspects of the invention.

The present invention uses uncommon substrates for the steps of Acylation. Present invention does not isolate the amine base. In the present invention it is the $NH_2HCl$ salt that is subjected to acylation. Reaction conditions are surprisingly different from those used in the prior art for Acylation. Besides these fundamental difference, there resides another fundamental difference in the reaction of N-Boc protection carried out in the prior art and in the present invention. Duration of the reaction in the present invention are surprisingly shorter.

In case of amidation reaction present invention does not use sub-zero temperatures whereas prior art reaction is carried out at sub-zero temperatures. Further the reagents used in the present invention are different, milder and environment friendly and hence surprisingly different from those used in the prior art.

Some reaction schemes have used N-acyl serine which the present invention does not use.

Prior art reactions have used volatile and detrimental or carcinogenic Methyl iodide for O-Methylation. Prior art reactions use costly reagent Silver Oxide. Silver Oxide also causes skin coloration if it contacts skin. These hazardous, carcinogenic and costly reagents are not used by present invention. Surprisingly although the reaction step is O-Methylation, the reaction conditions in the present invention are surprisingly different from those used in the prior art. Present invention does not use sub-zero temperatures.

Novelty and non-obviousness is imparted to the process by the facts of surprisingly different process conditions employed and by the fact of not isolating the free base of $NH_2HCl$ salt. Even when the free base of $NH_2HCl$ salt is not isolated, the reactions proceeds well and ultimately provides Lacosamide of desired purity, that too at lower costs. It is a common principle that when surprisingly different process conditions are used the process becomes novel and non-obvious.

These aspects of the present invention substantially increase the inherent utility of the invention.

Thus present invention is not only novel, non-obvious over prior art but it has tremendous utility and industrial application.

The term "Lacosamide" as used herein refers to the R-enantiomeric form of 2-acetamido-N-benzyl-3-methoxy-propionamide.

As used herein the term "ambient temperature" refers to 25-30° C. The term "Boc" refers to tert-Butyloxycarbonyl group, the term "NaOH" refers to Sodium hydroxide, the term "$PhCH_2NH_2$" refers to Benzyl amine, the term "$Me_2SO_4$" refers to Dimethyl sulphate, the term "KOH" refers to Potassium hydroxide, the term "HCl" refers to Hydrochloric acid, the term "MeOH" refers to Methanol, the term "$Ac_2O$" refers to Acetic anhydride, the term "DCM" refers to Dichloromethane.

While the present invention has been described in terms of its specific aspects, certain modifications and equivalents will be apparent to those skilled in the art and are intended to be included within the scope of the present invention.

Overall yield of the process provided by present invention is better than overall yield of the prior art processes. Overall yield was observed to be about 56%.

The chiral purity of the Lacosamide produced by the process of the present invention is about 100% ee.

Following section describes and illustrates the invention by way of examples. However, these do not limit the scope of the present invention. Several variants of these examples would be evident to persons ordinarily skilled in the art.

The main advantages of this invention are:
i) Overall yield is very high (>55%).
ii) The entire process is carried out in just two stages thus avoiding the material loss occurring during isolation of the intermediates.
iii) Boc-protection of D-serine has been reported in the literature at room temperature, which takes around 16-20 hours. In example 30 of U.S. Pat. No. 8,907,132, scheme 7, page 5-6, N-Boc-D-serine was prepared at 20-25° C. after stirring for 10 hours. Surprisingly it was found that the reaction could be carried out in just 1-2 h if the reaction temperature is maintained at 50° C. This modification has special advantage for large scale production as it will save considerable amount of reactor time.
iv) The conversion of N-Boc-D-serine (XII) to intermediate XXI has been carried out by literature references at −20 to 0° C. using isobutyl chloroformate as the alkyl chloroformate. It was noticed that the use of isobutyl chloroformate results in the formation of emulsion during workup. It was surprisingly observed that there is no emulsion formation during the work up when ethyl chloroformate was used in place of isobutyl chloroformate. The present invention thus surprisingly resolved the issues hindering the scalability of this reaction. Additionally, the reaction could be carried out at 10-15° C. instead of 0° C. or subzero temperatures.
v) O-methylation using dimethyl sulfate is usually carried out at temperatures around 0° C. The present invention reveals the conditions under which this reaction can be carried out at 10-15° C. This makes the process even more robust for the industrial production of Lacosamide on large scale.
vi) The present invention reveals direct N-acetylation on the hydrochloride salt intermediate in presence of an inorganic salt such as sodium acetate. Prior art references teach or disclose the use of base which is used to generate the free base intermediate (XII), which subsequently undergoes N-acetylation to give Lacosamide. Present invention avoids the use of base to neutralize the hydrochloride salt, and thus avoids the issues resulting from the unstable nature of the free base intermediate XII generated before acylation. This further improves the efficiency of the process as the product is obtained in purer form which can be easily purified to obtain pure Lacosamide.

The process provided by present invention does not use hazardous, pyrophoric, flammable reagents and cryogenic conditions. The process also does not use sub-zero temperatures and thus supports the large scale production of Lacosamide.

EXAMPLES

Example-1: Preparation N-Boc-D-Serine

To a solution of D-serine (150 g, 1.427 mol) and NaOH (68.5 g, 1.712 mol) in water (225 mL) was added di-tert-butyl dicarbonate (393.5 g, 1.712 mol) with stirring. The reaction mixture was heated to 50° C. for 1-2 h (the initial clear reaction mass turns turbid in 1-2 h). The mixture was cooled to room temperature and diluted with of water (900 ml). The reaction mixture was washed with ethyl acetate (2×300 mL) to get rid of the traces of unreacted D-serine and other minor impurities. The pH of the reaction mixture was adjusted to 3-4 by slow addition of cold 3N HCl (200 mL). The aqueous layer was extracted with ethyl acetate (3×400 mL). The combined organic layers of Boc-D-serine were washed with brine solution (300 mL) and used for the next stage.

Example-2: Preparation of tert-butyl[(2R)-1-(benzylamino)-3-hydroxy-1-oxopropan-2-yl]carbamate The above solution of N-Boc-D-serine (1.427 mol) was cooled to 10-15° C. and ethyl chloroformate (136 ml, 1.427 mol) was added followed by N-methylmorpholine (157 ml, 1.427 mol) and slow addition of benzylamine (156 ml, 1.427 mol) over a period of 2 h. After complete addition the reaction was stirred for additional 1 h and quenched by the addition of water (400 ml). The layers were separated and the organic layer was washed with 1N HCl solution, 5% sodium bicarbonate solution and 20% brine solution (300 ml each). The organic layer was evaporated under reduced pressure and the product was crystallized using ethyl acetate (300 ml) and n-Heptane (1200 ml). The product was filtered and dried in air oven at 50° C. to obtain 320 g (76.25%, 2 steps) of tert-butyl [(2R)-1-(benzylamino)-3-hydroxy-1-oxopropan-2-yl]carbamate.

Analysis:
Mass: 295 (M+1)
$^1$H NMR (CDCl$_3$): δ 8.31 (t, 1H), 7.20-7.31 (m, 5H), 6.66 (d, 1H), 4.85 (t, 1H), 4.29 (dd, 2H), 4.00 (dd, 1H), 3.56-3.61 (m, 2H), 1.39 (s, 9H).
$^{13}$C NMR (CDCl$_3$): δ 170.44, 155.19, 139.36, 128.10, 126.90, 126.58, 78.14, 61.79, 56.97, 41.95, 28.14.
Purity as determined by HPLC: 99.73%. Yield=75.7%

Example-3: Preparation of tert-butyl [(2R)-1-(benzylamino)-3-methoxy-1-oxopropan-2-yl]carbamate A solution of tert-butyl [(2R)-1-(benzylamino)-3-hydroxy-1-oxopropan-2-yl]carbamate (300 g, 1.019 mol) in methylene chloride (1500 ml) was cooled to 10-15° C. and potassium hydroxide (102.7 g, 1.834 mol) was added maintaining the temperature below 15° C. Dimethyl sulfate (218.38 g, 1.733 mol) was added below 15° C. in 10-15 min. The resulting mixture was stirred for 3-5 h at room temperature and water (1200 ml) was added. The layers were separated and the organic layer was evaporated under reduced pressure to obtain tert-butyl [(2R)-1-(benzylamino)-3-methoxy-1-oxopropan-2-yl]carbamate in oil form having HPLC purity more than 90%. This material was used in the next step without further purification.

Example-4: Preparation of Lacosamide

A solution of tert-butyl [(2R)-1-(benzylamino)-3-methoxy-1-oxopropan-2-yl]carbamate (1.019 mol) obtained in Example 3 in methanol (300 ml) was heated at 50° C. with and Methanolic HCl (300 ml, 10%) was added under stirring. The reaction mixture was stirred at 50° C. for 2 h, evaporated under reduced pressure. Methanol (300 ml) was added to the residue and evaporated under reduced pressure to provide HCl salt of O-methyl-N-benzyl-D-serinamide in oil form having HPLC purity more than 90%.

The above HCl salt of O-Methyl-N-benzyl-D-Serinamide (1.019 mol) was dissolved in methylene dichloride at room temperature and sodium acetate (125.4 g, 1.529 mol) was added under stirring. Acetic anhydride (127.05 g, 1.223 mol) was added slowly and stirred for 2-3 h. The reaction mass was washed with water (1200 ml) and the layers were separated. The organic layer was evaporated under reduced pressure and the residue was subjected to precipitation by dissolving in Ethyl acetate (2700 ml) and adding n-Heptane (3300 ml). The precipitated solid was filtered under reduced pressure to obtain crude Lacosamide having HPLC purity more than 98%.

Example-5: Purification of Lacosamide

The crude Lacosamide obtained in Example-4 was dissolved in Ethyl acetate (1200 ml) and the mixture was heated to 55° C. n-Heptane (1200 ml) was added and the mixture was stirred for additional 30-40 min at 55° C. The reaction mixture was cooled to 50° C. and stirred for 2 h. The precipitate was filtered under reduced pressure and washed with cold 1:1 mixture of ethyl acetate and n-heptane (300 ml). The solid was dried under vacuum at 50° C. to obtain Lacosamide.

Analysis:
Mass: 251 (M+1)
$^1$H NMR (CDCl$_3$): δ 8.48 (t, 1H), 8.08 (d, 1H), 7.18-7.34 (m, 5H), 4.49 (dd, 1H), 4.29 (d, 2H), 3.47-3.55 (m, 2H), 3.25 (s, 3H), 1.87 (s, 3H).
$^{13}$C NMR (CDCl$_3$): δ 69.72, 169.37, 139.26, 128.15, 126.92, 126.62, 72.09, 58.15, 52.62, 41.98, 22.52.
Purity by HPLC: 99.94%. Yield=77.3%. Chiral Purity=100% ee

We claim:
1. A process for the preparation of Lacosamide comprising:
   i) N-Boc protection of D-serine at 50° C. for the duration of 1-2 hours using Boc-anhydride in the presence of sodium hydroxide as a base and water as a solvent to obtain N-Boc-D-serine,
   ii) coupling of the carboxylic acid moiety of the N-Boc-D-serine produced in step i), with benzyl amine in the presence of ethyl chloroformate and N-methyl morpholine at 10 to 15° C. to obtain tert-butyl [(2R)-1-(benzyl amino)-3-hydroxy-1-oxopropan-2-yl]carbamate,
   iii) O-methylation of the tert-butyl [(2R)-1-(benzyl amino)-3-hydroxy-1-oxopropan-2-yl]carbamate produced in step ii), with dimethyl sulfate in the presence of potassium hydroxide as a base and dichloromethane as a solvent and in the absence of a phase transfer catalyst (PTC), to generate tert-butyl [(2R)-1-(benzylamino)-3-methoxy-1-oxopropan-2-yl]carbamate,
   iv) hydrolysis of the N-Boc group of the tert-butyl [(2R)-1-(benzylamino)-3-methoxy-1-oxopropan-2-yl]carbamate produced in step iii) with an alcoholic HCl at 50° C. to produce a hydrochloride salt of (R)-2-amino-N-benzyl-3-methoxypropanamide and subsequent N-acetylation of the hydrochloride salt of (R)-2-amino-N-benzyl-3-methoxypropanamide in the presence of sodium acetate without isolating free base (R)-2-amino-N-benzyl-3-methoxypropanamide, to produce Lacosamide.

2. The process according to claim 1, wherein the O-methylation in step iii) is carried out at 10-15° C.

3. The process according to claim 1, wherein the alcoholic HCl in step iv) is selected from the group consisting of methanolic HCl, ethanolic HCl, propanolic HCl, and isopropanolic HCl.

4. The process according to claim 1, wherein the N-acetylation of the hydrochloride salt in step iv) is done using sodium acetate and acetic anhydride at ambient temperature.

5. The process according to claim 1, further comprising purification of Lacosamide produced in step iv) using an ethyl acetate:n-heptane solvent mixture at 50-55° C.

6. The process according claim 5, wherein the volume ratio of ethyl acetate:n-heptane ranges from 2:1 to 1:2.

* * * * *